(12) United States Patent
Wang et al.

(10) Patent No.: US 8,524,658 B2
(45) Date of Patent: *Sep. 3, 2013

(54) LACTOFERRIN AND BRAIN HEALTH AND DEVELOPMENT IN INFANTS

(75) Inventors: Bing Wang, Tianjin (CN); Magali Faure, Forel (CH); Jeroen Schmitt, Moudon (CH)

(73) Assignee: Nestec S.A., Vevey (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/319,661

(22) PCT Filed: May 7, 2010

(86) PCT No.: PCT/EP2010/056237
§ 371 (c)(1),
(2), (4) Date: Jan. 12, 2012

(87) PCT Pub. No.: WO2010/130643
PCT Pub. Date: Nov. 18, 2010

(65) Prior Publication Data
US 2012/0184484 A1    Jul. 19, 2012

(30) Foreign Application Priority Data
May 12, 2009 (EP) ..................... 09159966

(51) Int. Cl.
*A01N 37/18* (2006.01)
*A61K 38/40* (2006.01)
*A61K 47/48* (2006.01)
*C07K 14/79* (2006.01)

(52) U.S. Cl.
USPC ........................................ 514/2.5

(58) Field of Classification Search
USPC ........................................ 514/102
See application file for complete search history.

(56) References Cited

U.S. PATENT DOCUMENTS

| | | | |
|---|---|---|---|
| 7,368,141 B2 * | 5/2008 | Lihme | 426/531 |
| 2002/0004073 A1 | 1/2002 | Gohlke et al. | |
| 2007/0009609 A1 | 1/2007 | Gohlke et al. | |
| 2008/0064635 A1 * | 3/2008 | Rueda et al. | 514/12 |

FOREIGN PATENT DOCUMENTS

| | | |
|---|---|---|
| CN | 101279866 | 10/2008 |
| IE | 20060795 | 5/2007 |
| JP | 8038044 | 2/1996 |
| JP | 2006006257 | 1/2006 |
| WO | WO2007145220 | 12/2007 |
| WO | WO 2007145520 A1 * | 12/2007 |
| WO | WO2008005033 | 1/2008 |
| WO | WO2008018103 | 2/2008 |

OTHER PUBLICATIONS

Otsuki et al. "Effect of enteric-coated lactoferrin on constipation during pregnancy" Biochemistry and Cell Biology, Biochinie et Biologie Cellulaire, vol. 84, No. 3, Jun. 2006, p. 394, Abstract, XP008112904.
Lonnerdal BO "Nutritional roles of lactoferrin", Current Opinion in Clinical Nutrition and Metabolic Care, vol. 12, No. 3, May 2009, pp. 293-297, XP008105975.
Lin et al. "Human lactoferrin exerts bi-directional actions on PC12 cell survival via ERK½ pathway", Neuroscience, vol. 151, No. 2, Jan. 2008, pp. 396-402, XP005093452.
Postuma et al. "Effects of the amyloid protein precursor of Alzheimer's disease and other ligands of the LDL receptor-related protein on neurite outgrowth from sympathetic neurons in culture", FEBS Letters, vol. 428, No. 1-2, May 1998, pp. 13-16, XP004257902.
Youdim et al. "Putative biological mechanisms of the effect of iron deficiency on brain biochemistry and behavior", The American Journal of Clinical Nutrition, vol. 50, No. 3, Sep. 1989, pp. 607-615, XP008113294.
Takeuchi et al. "Opioid mediated suppressive effect of milk-derived lactoferrin on distress induced by maternal separation in rat pups", Brain Research. vol. 979, No. 1-2, Jul. 2003, pp. 216-224, XP002550200.
Talukder et al. "Receptor-mediated transport of lactoferrin into the cerebrospinal fluid via plasma in young calves", Journal of Veterinary Medical Science, vol. 65, No. 9, Sep. 2003, pp. 957-964, XP008113239.
Lin et al. "Bovine lactoferrin protects RSC96 Schwann cells from tumor necrosis factor-alpha-induced growth arrest via extracellular-signal-regulated kinase ½", Neuroscience, vol. 151, No. 2, Jan. 2008, pp. 396-402, XP022416156.
Shoji et al., Effect of Iron-Unsaturated Human Lactofferin on Hydrogen Peroxide-Induced Oxidative Damage in Intestinal Epithelial Cells, Pediatric Research, vol. 61, No. 1, 2007, pp. 89-92, XP002548906.

* cited by examiner

*Primary Examiner* — Marcela M Cordero Garcia
*Assistant Examiner* — Kaipeen Yang
(74) *Attorney, Agent, or Firm* — K&L Gates LLP

(57) ABSTRACT

The present invention relates generally to the field of brain development and brain health. One embodiment of the present invention relates to a composition that can be used for the treatment or prevention of a delayed brain development and/or a delayed development of the nervous system. Also cognitive performance can be increased.

13 Claims, 9 Drawing Sheets

LACTOFERRIN AND BRAIN HEALTH AND DEVELOPMENT IN INFANTS

CROSS REFERENCE TO RELATED APPLICATIONS

The present application is a National Stage of International Application No. PCT/EP2010/056237, filed on May 7, 2010, which claims priority to European Patent Application No. 09159966.2, filed on May 12, 2009, the entire contents of which are being incorporated herein by reference.

The present invention relates generally to the field of brain health, brain protection and brain development. One embodiment of the present invention relates to a composition that can be used for the treatment or prevention of a delayed brain development and/or a delayed development of the nervous system. Neuronal cells in the brain can be protected. Also cognitive performance can be increased.

Mother's milk is recommended for all infants. However, in some cases breast feeding is inadequate or unsuccessful or inadvisable for medical reasons or the mother chooses not to breast feed either at all or for a period of more than a few weeks. Infant feeding formulas have been developed for these situations. Infant feeding formulas are commonly used today to provide supplemental or sole source nutrition early in life. They may be used instead of or in addition to mother's milk to feed infants. Consequently, they are often designed today to resemble mother's milk as closely as possible in terms of composition and function.

Recently, evidence is accumulating that breastfeeding may provide long-term cognitive advantages, particularly for infants born small or premature (Anderson et al., Am J Clin Nutr 1999; 70:525-35; Lucas et al., Lancet 1992; 339:261-4). However, the underlying mechanism to explain the relationship between breastfeeding and cognitive development remains unclear.

It has been suggested that docohexanoic acid (DHA) and arachidonic acid (AA) that are present in human milk might play a role in the observed effect.

A further study claims that dietary sialic acid supplementation improves learning and memory in piglets (Wang et al., 2007, American Journal of Clinical Nutrition, Vol. 85, No. 2, 561-569). Sialic acid is known to be a key component of both human milk oligosaccharides and neural tissues.

The nervous system is a highly complex network composed of neuronal and glial cells. It is present in all mammalian species. The nervous system is composed of the central nervous system (brain and spinal cord) and the peripheral nervous system (somatic, autonomous and enteric nervous system). The central nervous system drives the cognitive functions (memory, attention, perception, action, etc). Together with the peripheral nervous system, it has a fundamental role in the control of behaviour.

The nervous system develops during gestation and then refines to a mature, functional network during the post natal period. Immaturity or delayed maturation of the nervous system leads to delayed establishment of the important biological functions that it regulates. For example, this may lead to a delayed establishment of cognitive functions (learning ability, attention, etc).

It is commonly accepted that cognitive development and cognitive performance have a significant influence on the quality of life. It would hence be desirable to have available a composition that allows supporting the development and performance of the nervous system and of the brain.

It was consequently an object of the present invention to improve the state of the art and to provide a composition that is based on natural ingredients and that allows supporting the development and performance of the nervous system and of the brain, in particular of infants, for example IUGR infants.

This object was achieved by the subject matter of the independent claims.

The present inventors were able to demonstrate that lactoferrin, for example a composition supplemented with lactoferrin, can be used to improve brain development and cognitive functioning.

It could further be shown that the administration of lactoferrin allows it to increase the neuron density and neuron survival.

Metabolic changes in the hippocampus measured by MRS after lactoferrin administration imply that learning and short term memory is modulated.

Metabolic changes in the cortex after lactoferrin administration imply that long term memory is modulated.

Lactoferrin (LF), also known as lactotransferrin (LTF), is a globular multifunctional protein that is known to exhibit an antimicrobial activity and is a part of the innate defense, mainly at mucoses.

Lactoferrin may be found for example in milk and whey and in many mucosal secretions such as tears and saliva. As such, Lactoferrin may be purified, e.g., from milk or may be produced recombinantly.

The present invention relates to lactoferrin obtainable from any source.

Lactoferrin from milk or whey, for example, has the advantage that it is a natural ingredient obtained from a food-grade composition and can consequently be used as enriched fraction of the food composition without further purification.

Recombinantly obtained lactoferrin has the advantage that it can be produced easily in high concentrations.

Human colostrum has a relatively high concentration of lactoferrin, followed by human milk, then cow milk.

The composition of the present invention can be in particular effective in IUGR mammals. Intrauterine Growth Restriction (IUGR) is a term used to describe a condition in which the fetus or infant is smaller than expected for the number of weeks of pregnancy. A fetus or infant with IUGR often has a weight that is reduced by at least 10% compared to normal fetusses or infants of the same gestational age. For example a human fetus with IUGR may be born at term (after 37 weeks of pregnancy) or prematurely (before 37 weeks).

The present inventors have found that lactoferrin or lactoferrin enriched compositions may be used to protect neuronal cells against degeneration. Such a degeneration may follow, for example, stress. Lactoferrin was found to promote neuronal survival and/or limit or prevent neuronal death in the brain.

In infants the lactoferrin and/or the lactoferrin containing compositions of the present inventions may be used to protect the central nervous system from any stress occurring during the neuronal development period, and—consequently—to limit and/or prevent stress-induced neuronal growth retardation and associated cognitive dysfunctions.

For the purpose of the present invention, the term "infant" includes children and comprises subjects in the age range from 0-14 years.

A human infant less than a month old is a newborn or a neonate. The term "newborn" includes premature infants, postmature infants and full term newborns. Upon reaching the age of one or beginning to walk, infants are also referred to as "toddlers" (generally 12-36 months).

Lactoferrin and/or the composition of the present invention may be administered for example to premature or term-born infants having experienced an intrauterine growth retardation that may occur following any adverse events during the gestation (smoking of the mother, medication of the mother, low placenta quality, abnormal placenta positioning, malnutrition of the mother and the fetus, etc)

Premature infants without any intrauterine growth retardation

Very low/low birth weight infants

IUGR infants

Neonates and children showing brain growth retardation following for example hypoxemia-ischemia at birth or any other adverse event Neonates and children showing cognitive disfunctions, retardation Lactoferrin or the composition of the present invention can therefore be administered to the infant and/or to the mother during the gestation and/or lactation period.

Consequently, one embodiment of the present invention is an ingestible composition enriched in lactoferrin.

Enriched means that lactoferrin was either added to the composition, so that the resulting lactoferrin content of the composition is higher than the lactoferrin content of the composition without lactoferrin addition, or that the composition was treated in a way to concentrate the natural lactoferrin content in a composition.

Lactoferrin may also be provided as pure compound.

Alternatively, lactoferrin may be provided as a lactoferrin enriched fraction, for example a lactoferrin enriched milk or whey fraction.

As milk or whey source bovine milk, human milk, goat milk, camel milk, horse milk and/or donkey milk may be used, for example. Colostrum may be used as well.

In therapeutic applications, compositions are administered in an amount sufficient to at least partially cure or arrest the symptoms of the disorder and/or its complications. An amount adequate to accomplish this is defined as "a therapeutically effective dose". Amounts effective for this purpose will depend on a number of factors known to those of skill in the art such as the severity of the disorder and the weight and general state of the patient. In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

Lactoferrin may be administered in the framework of the present invention in a therapeutically effective dose and/or in a prophylactic effective dose.

Typical lactoferrin enriched compositions may comprise lactoferrin in an amount of at least 1.6 g/L.

For example, the composition of the present invention may contain lactoferrin in a concentration of at least 0.75% (w/w), preferably at least 1% (w/w).

In one embodiment, the composition is to be administered in an amount corresponding to an ingestion of at least 0.25 g lactoferrin, preferably at least 0.5 g lactoferrin more preferably at least 1 g lactoferrin per day per kg body weight.

For example, the composition may be consumed in an amount corresponding to at least 1 g lactoferrin/kg body weight/day intake for pregnant and/or lactating mothers.

The composition may also be consumed in an amount corresponding to at least 200 mg lactoferrin/kg body weight/day intake for the children.

Lactoferrin may be present in the composition in a concentration of at least 0.01 g per 100 kcal, preferably of at least 0.1 g per 100 kcal. For example, lactoferrin may be present in the composition in the range of about 0.01 g-100 g, preferably 0.1 g-50 g, even more preferred 2 g-25 g per 100 kcal of the composition.

Lactoferrin may also be used in combination with other compounds, such as sialic acid and/or iron, for example.

A particular preferred lactoferrin containing composition may contain additionally sialic acid in an amount in the range of 100 mg/100 g (w/w) to 1000 mg/100 g (w/w) of the composition, for example in the range of 500 mg/100 g (w/w) to 650 mg/100 g (w/w) of the composition.

The composition of the present invention may for example comprise at least about 0.001 weight-% sialic acid. In further embodiments of the present invention, the composition may comprise at least about 0.005 weight-%, or at least about 0.01 weight-% of sialic acid.

Alternatively or additionally the lactoferrin containing composition may contain iron in an amount in the range of about 1 mg/100 g (w/w) to 50 mg/100 g (w/w) of the composition, for example 10 mg/100 g (w/w) to 30 mg/100 g (w/w) of the composition.

One lactoferrin containing composition may contain for example about 852 mg/100 g (w/w) sialic acid and 22 mg/100 g (w/w) iron.

The lactoferrin containing composition of the present invention may have a caloric density in the range of 30 kcal/100 g-1000 kcal/100 g of the composition, preferably 50 kcal/100 g-450 kcal/100 g of the composition. It may for example have a caloric density of about 400 kcal/100 g.

The nature of the composition is not particularly limited. It is preferably a composition for oral or enteral administration.

The composition may be for example selected from the group consisting of food products, animal food products, pharmaceutical compositions, nutritional formulations, nutraceuticals, drinks, food additives, and infant feeding formulas.

In one typical embodiment of the present invention, the composition will contain a protein source, a lipid source and a carbohydrate source.

For example such a composition may comprise protein in the range of about 2 to 6 g/100 kcal, lipids in the range of about 1.5 to 3 g/100 kcal and/or carbohydrates in the range of about 1.7 to 12 g/100 kcal If the composition is liquid, its energy density may be between 60 and 75 kcal/100 ml.

If the composition is solid, its energy density may be between 60 and 75 kcal/100 g.

The type of protein is not believed to be critical to the present invention. Thus, protein sources based on whey, casein and mixtures thereof may be used, for example. As far as whey proteins are concerned, acid whey or sweet whey or mixtures thereof may be used as well as alpha-lactalbumin and beta-lactoglobulin in whatever proportions are desired. The whey protein may be modified sweet whey. Sweet whey is a readily available by-product of cheese making and is frequently used in the manufacture of infant formulas based on cows' milk. However, sweet whey includes a component which is undesirably rich in threonine and poor in tryptophan called caseino-glyco-macropeptide (CGMP). Removal of the CGMP from sweet whey results in a protein with a threonine content closer to that of human milk. This modified sweet whey may then be supplemented with those amino acids in respect of which it has a low content (principally histidine and tryptophan). A process for removing CGMP from sweet whey is described in EP 880902 and an infant formula based on this modified sweet whey is described in WO 01/11990. The proteins may be intact or hydrolysed or a mixture of intact and hydrolysed proteins. It may be desirable to supply partially hydrolysed proteins (degree of hydrolysis between 2 and 20%), for example for subjects believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in two steps as described in EP 322589. For an extensively hydrolysed protein, the whey proteins may be subjected to triple hydrolysis using Alcalase 2.4 L (EC 940459), then Neutrase 0.5 L (obtainable from Novo Nordisk Ferment AG) and then pancreatin at 55° C. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The compositions of the present invention may contain a carbohydrate source. Any carbohydrate source may be used, such as lactose, saccharose, maltodextrin, starch and mixtures thereof.

The compositions of the present invention may contain a lipid source. The lipid source may be any lipid. Preferred fat sources include milk fat, palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. The lipid source preferably has a ratio of n-6 to n-3 fatty acids of about 5:1 to about 15:1; for example about 8:1 to about 10:1.

The compositions of the present invention may also contain all vitamins and minerals understood to be essential in the daily diet and in nutritionally significant amounts.

Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the numerous factors, such as age weight and condition of the person or animal the composition is administered to.

The compositions may also comprise at least one probiotic bacterial strain. A probiotic is a microbial cell preparation or components of microbial cells with a beneficial effect on the health or well-being of the host. Suitable probiotic bacterial strains include *Lactobacillus rhamnosus* ATCC 53103 obtainable from Valio Oy of Finland under the trade mark LGG, *Lactobacillus rhamnosus* CGMCC 1.3724, *Lactobacillus paracasei* CNCM I-2116, *Lactobacillus reuteri* ATCC 55730 and *Lactobacillus reuteri* DSM 17938 obtainable from BioGaia AB, *Bifidobacterium lactis* CNCM I-3446 sold inter alia by the Christian Hansen company of Denmark under the trade mark Bb12 and *Bifidobacterium longum* ATCC BAA-999 sold by Morinaga Milk Industry Co. Ltd. of Japan under the trade mark BB536. The amount of probiotic, if present, likewise preferably varies as a function of the age of the person or animal. Generally speaking, the probiotic content may increase with increasing age of the infant for example from $10^3$ to $10^{12}$ cfu/g formula, more preferably between $10^4$ and $10^8$ cfu/g formula (dry weight).

The compositions may also contain at least one prebiotic in an amount of 0.3 to 10%. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®.

A particularly preferred prebiotic is a mixture of galacto-oligosaccharide(s), N-acetylated oligosaccharide(s) and sialylated oligosaccharide(s) in which the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture. This mixture is hereinafter referred to as "CMOS-GOS". Preferably, a composition for use according to the invention contains from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide.

Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828. Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc.

Synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc, Galβ1,4Galβ1,4Glc and Galβ1,4Galβ1,4Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

Suitable sialylated oligosaccharides include NeuAcα2,3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

The compositions may optionally contain other substances which may have a beneficial effect such as nucleotides, nucleosides, and the like.

The compositions, for example an infant formula, for use in the invention may be prepared in any suitable manner. For example, an infant formula may be prepared by blending together the protein source, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger. The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point. The homogenised mixture is transferred to a suitable drying apparatus such as a spray drier or freeze drier and converted to powder. The powder should have a moisture content of less than about 5% by weight. If it is desired to add probiotic(s), they may be cultured according to any suitable method and prepared for addition to the infant formula by freeze-drying or spray-drying for example. Alternatively, bacterial preparations can be bought from specialist suppliers such as Christian Hansen and Morinaga already prepared in a suitable form for addition to food products such as infant formula. Such bacterial preparations may be added to the powdered infant formula by dry mixing.

Lactoferrin may be added at any stage during this procedure, but is preferably added after the heating step.

The composition comprises a protein source which may be present in the range of between 1.4 and 100 g/100 kcal, preferably between 1.4 and 6.0 g/100 kcal of the composition. Since lactoferrin is a protein it should be considered a part of the protein source.

Whey protein is known to provide several health benefits. For example, it is easily digestible. The protein fraction in whey (approximately 10% of the total dry solids within whey) comprises several protein fractions, for example beta-lactoglobulin, alpha-lactalbumin, bovine serum albumin and immunoglobulins. In one embodiment at least 50%, preferably at least 75%, even more preferred at least 85% by weight of the protein source is whey protein.

If present, the lipid source may contribute to between 30 to 55% of the total energy of the composition. A carbohydrate source may contribute to between 35 and 65% of the total energy of the composition.

Sialic acid may also be added to the composition of the present invention. Sialic acid is a generic term for the N- or O-substituted derivatives of neuraminic acid, a monosaccharide with a nine-carbon backbone.

Any sialic acid may be used for the purposes of the present invention. However, it is preferred if the sialic acid has the following formula

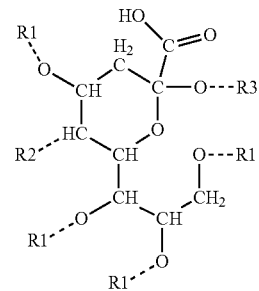

R1=H, acetyl, lactyl, methyl, sulfate, phosphate, anhydro, sialic acid, fucose, glucose, or galactose R2=N-acetyl, N-glycolyl, amino, hydroxyl, N-glycolyl-O-acetyl, or N-glycolyl-O-methyl R3=H, galactose, N-acetylglucosamine, N-acetylgalactosamine, sialic acid, or N-glycolylneuraminic acid R1 may be selected from the group consisting of H, acetyl, lactyl, methyl, sulfate, phosphate, anhydrosialic acid, fucose, glucose and/or galactose.

R2 may be selected from the group consisting of N-acetyl, N-glycolyl, amino, hydroxyl, N-glycolyl-O-acetyl, and/or N-glycolyl-O-methyl.

R3 may be selected from the group consisting of H, galactose, N-acetylglucosime, N-acetylgalactosamine, sialic acid, and/or n-glycolylneuraminic acid.

The groups in position R1 may be identical or may differ from each other.

For example, the sialic acid may be N-acetylneuraminic acid with R1=H, R2=N-acetyl and R3=H. According to a further embodiment of the present invention the sialic acid may selected from the group consisting of 2-keto-5-acetamido-3,5-dideoxy-d-glycero-d-galactononulosonic acid (Neu5Ac) and n-glycolylneuraminic acid or mixtures thereof.

Sialic acid as used in the present invention comprises N-Acetylneuraminic acid, which has the following synonyms and abbreviations: o-Sialic acid; 5-Acetamido-3,5-dideoxy-D-glycero-D-galacto-2-non ulosonic acid; 5-Acetamido-3,5-dideoxy-D-glycero-D-galactonulosonic acid; Aceneuramic acid; N-acetyl-neuraminate; N-Acetylneuraminic acid; NANA, and Neu5Ac.

The present invention extends to the use of lactoferrin for the preparation of a composition for the treatment or prevention of a delayed brain development and/or a delayed development of the nervous system.

For the uses of the present invention it is essential that the composition contains lactoferrin or a compound that yields lactoferrin after consumption. The composition does not have to be enriched in lactoferrin, although this may be preferable, since this way more lactoferrin can be administered in smaller volumes.

The lactoferrin may be used to prepare any kind of composition. It is preferred, however, that the lactoferrin is provided as a composition in accordance with what is described above.

In one embodiment of the present invention, the lactoferrin containing composition may be used to treat or prevent a delayed vision development.

In another embodiment of the present invention, the lactoferrin containing composition may be used to treat or prevent a delayed neural migration.

In a further embodiment of the present invention, the lactoferrin containing composition may be used to treat or prevent a delayed cognitive development.

The composition of the present invention can be used to increase the neuronal density and or the neuronal survival.

The compositions of the present invention may further be used to treat or prevent an impaired learning ability, an impaired mental performance or a reduced attention span.

To achieve this, the composition may be administered to mothers during pregnancy, mothers during lactation, to premature or term born babies, to very low/low birth weight infants, IUGR infants, infants, toddlers, children and/or teenagers.

While the compositions of the present invention can generally be used to treat or prevent brain disorders and/or to repair and/or reverse brain damage in infants of any age group, it was found that the compositions of the present invention are particular helpful to treat or prevent brain disorders and/or to repair and/or reverse brain damage in IUGR infants.

Those skilled in the art will understand that they can freely combine all features of the present invention described herein, without departing from the scope of the invention as disclosed. In particular, features described for the uses of the present invention may be applied to composition of the present invention and vice versa.

Further advantages and features of the present invention are apparent from the following Examples and Figures.

FIG. 1 shows the percentage of positive NS20Y cells for neurite outgrowth in basal condition (untreated cells) and after treatment of the cells with either the neurotrophic factor CNTF (100 ng/mL, positive control) or the lactoferrin enriched bovine milk fraction at different concentrations. Data are means±SEM, n=3 to 7 according to the group (Basal, n=7; CNTF, n=3; 1 ug/L, n=3; 10 ug/L, n=7; 100 ug/L, n=3; 1 mg/L, n=3; 10 mg/L, n=5; 100 mg/L, n=7; 1 g/L, n=6). Data were compared to the basal untreated group with the student t test. A difference was considered significant when $P<0.05$.

FIG. 2 shows the release of neuron-specific enolase (NSE), a marker for neuronal cell death, by a primary culture of enteric neurons, following $H_2O_2$ challenge and prevention with bovine milk Lactoferrin. Data are mean±SEM, n=8. A difference was considered significant when $P<0.05$ FIG. 3 shows the percentage of 7-AAD positive cells in cultured SH-SY5Y cells, following $H_2O_2$ challenge in presence or not of different concentrations of bovine milk Lactoferrin ranging from 0.001 to 1 g/L.

EXAMPLES

Biological activity of lactoferrin enriched bovine milk fraction has an effect on promoting neuronal cell survival and neurite outgrowth in vitro The neurite outgrowth process comprises the outgrowth of axons from neurons and is part of neuronal development. The impact of a fraction of bovine milk enriched in lactoferrin on neurite outgrowth was measured using a well established and commonly used in vitro bioassay.

Briefly, NS20Y murine neuroblastoma cells (DSMZ) were thawed from cryogenic storage, plated at a density of approximately $27 \times 10^3$ cells per $cm^2$ in tissue culture-treated flasks (Falcon) and expanded in the presence of DMEM (Gibco) containing 10% FCS (Gibco) and 2 mM L-glutamine (Gibco). Two days after plating, the cells were detached from the flask by mechanical agitation (tapping of the flask), and a single cell suspension was obtained by passing the suspension several times through a flame-polished glass pipette. Cells were then plated onto 13 mm round glass coverslips in the presence of DMEM containing 10% FCS and 2 mM L-glutamine at a density of 2,000 cells per coverslip. The following day the medium was switched to DMEM containing 0.5% FCS, 2 mM L-glutamine, and different concentrations of the milk fractions to be tested. One day later cells were fixed with 4% paraformaldehyde and the coverslips mounted on slides.

All coverslips were imaged with an Axioplan 2 microscope (Zeiss). Digital images were taken from 25 defined fields across the diameter of the coverslip (20× objective, Axiocam MRc, Zeiss). Cells were counted systematically from the first field at the edge of the coverslip across the coverslip until 100 cells had been counted. Cells were scored for either positive or negative for neurite outgrowth. Positive cells for neurite outgrowth were considered if the axon-resembling projections emanating from the cell body reached a length greater than the cell body.

A student t test was used to compare differences in the mean between one control reference population and means from all other treatments in each group.

Figure 1:
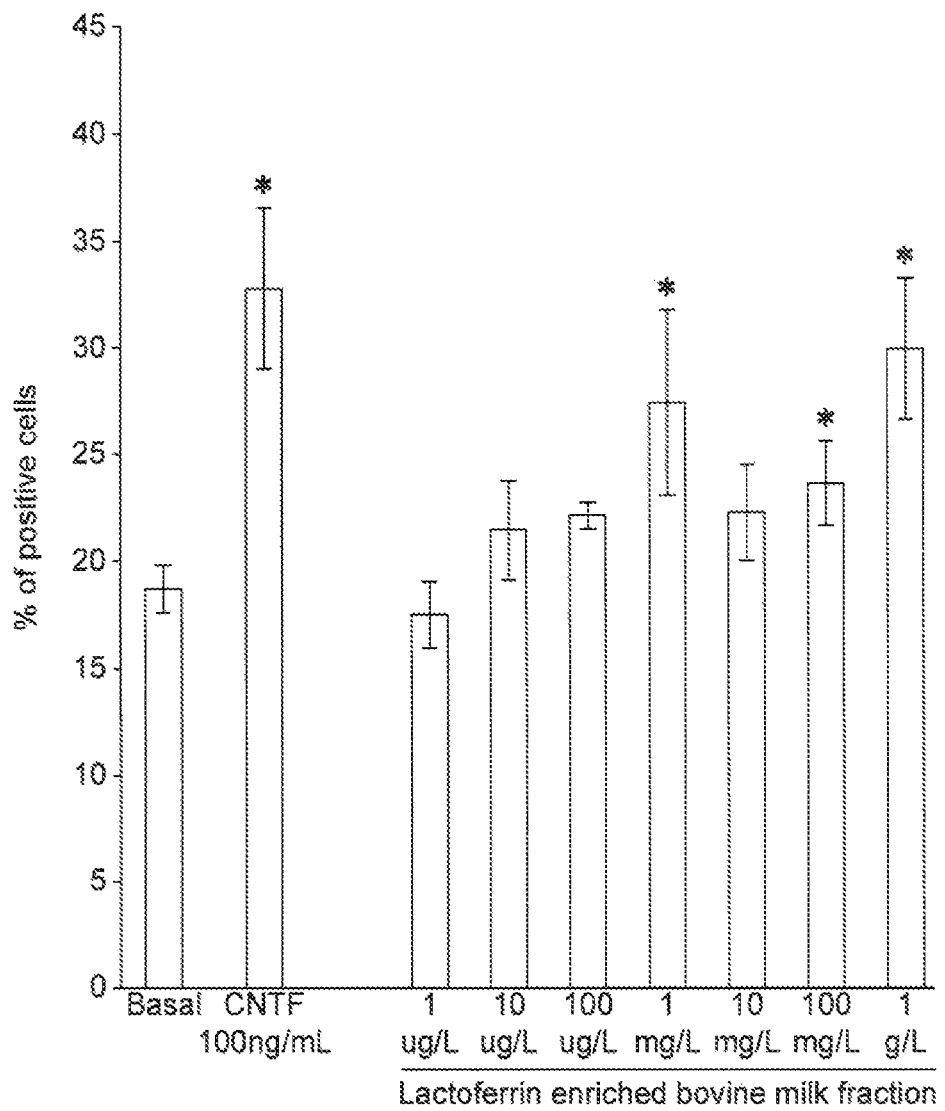

The following concentrations of the lactoferrin enriched bovine milk fraction were tested: 1 μg/L, 10 μg/L, 100 μg/L, 1 mg/L, 10 mg/L, 100 mg/L, and 1 g/L. A positive control (CNTF, ciliary neurotrophic factor, 100 ng/mL), which is a well known neurotrophic factor previously reported to promote neurite outgrowth of different neuronal populations (Oyesiku and Wigston, 1996 (Oyesiku N M, Wigston D J:

Ciliary neurotrophic factor stimulates neurite outgrowth from spinal cord neu-rons. J Comp Neurol 1996; 364: 68-77.) was performed. A basal control consisted of untreated cells. Results are shown in FIG. 1.

Protection of Neuronal Cells Against Stress

Figure 2:
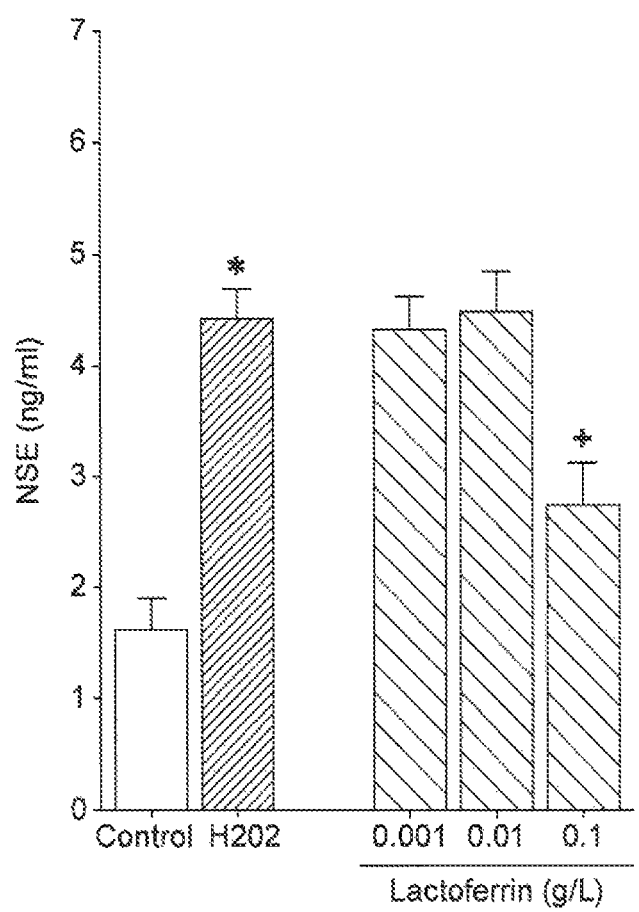

Rat primary cultures of enteric neuronal cells were seeded into wells and incubated with different concentrations of bovine lactoferrin-enriched fraction for 48 h. After washing three times with phosphate buffer saline (sterile PBS, 37° C.), the cells were incubated for 12 hours in cell medium without lactoferrin and containing $H_2O_2$ or its vehicle (control). The protective effect of lactoferrin upon $H_2O_2$-induced neuronal cell death was evaluated by measuring the release of neuron-specific enolase (NSE) in the cell medium. After oxidative stress, the medium of the different groups were collected and centrifuged for 10 min at 12,000 rpm (4° C.). The supernatant was collected and the NSE released in the culture medium was quantified by immunoradiometric assay. Results are expressed in ng/mL. As shown on FIG. 2, $H_2O_2$ induced a significant increase of NSE in the medium ($p<0.05$, $n=8$). Treatment of primary neuronal enteric cells with lactoferrin-enriched fraction significantly prevented the $H_2O_2$-induced release of NSE ($p<0.05$, $n=8$).

Figure 3:
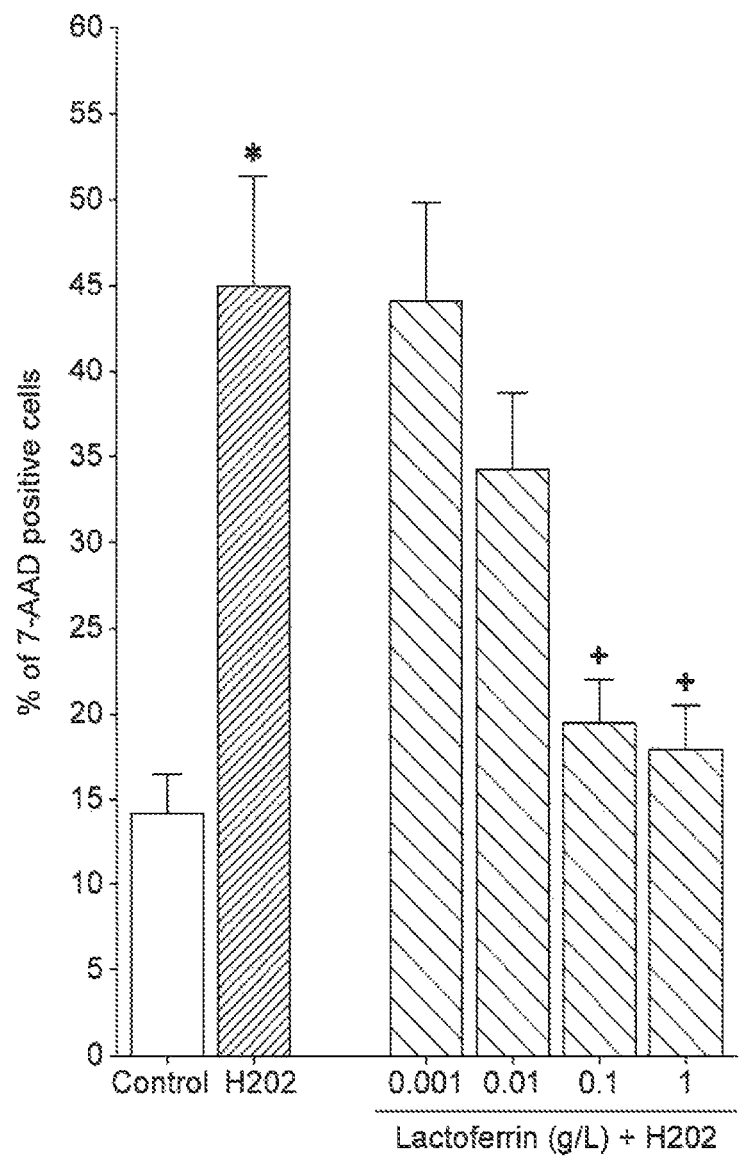

The neuroprotective property of bovine lactoferrin was confirmed using a human neuronal-like cell line (SH-SY5Y-neuroblastoma cells). Briefly, SH-SY5Y cells were plated for 24 h, and bovine lactoferrin-enriched fraction was added to the culture media of cells at different concentrations for the following 48 h. Cells were challenged with $H_2O_2$ for 6 h. Cells were finally washed with 0.1 M PBS before being harvested with trypsine-EDTA. Cell suspension was then pooled with the supernatant and centrifuged for 5 min at 2,000 rpm. After centrifugation, the pellet was resuspended in 500 microliter of PBS 0.1 M. Membrane permeability was evaluated by flow cytometry using the 7-AAD as fluorescent marker. For this, 200 microliter of cell suspension were incubated with 7-AAD for 10 min before acquisition using BD FACS Array™ bioanalyser. This flow cytometric assay using 7-aminoactinomycin D (7-AAD) allowed to distinguish live (7-AAD negative) and late apoptotic/necrotic (7-AAD positive) SH-SY5Y cells in response to oxidative stress. Results as presented in FIG. 3 were expressed as percentage of 7-AAD positive cells per total number of cells. As shown in FIG. 3, $H_2O_2$ induced a significant increase in the percentage of 7-AAD positive cells ($p<0.05$, $n=6$). Treatment of SH-SY5Y cells with lactoferrin prevented the $H_2O_2$-induced increase in percentage of 7-ADD positive cells.

Lactoferrin Improves the Brain/Body Weight Ratio in Normal and IUGR Infants

Rat Model: Wister Rat

Dams are treated with dexamethasone (DEX) during the third week of gestation. This corticosteroid will be delivered during the $3^{rd}$ of gestation by an osmotic pump Alzet® embedded subcutaneously; sham animals with osmotic pump containing saline buffer will be used as control. This design represents a model of high frailty for pups, mimicking a situation of frailty during the perinatal period in the human species, which is a property model to prove the ability of lactoferrin to enhance the brain development apart from any other interventions. Lactoferrin supplementation will be tested 1) during both gestation and lactation, 2) during lactation and 3) no supplementation. For establishing a logical experimental design allowing proper comparisons, the same supplementation protocol will be applied to normal gestations.

IUGR pups: model of intrauterine growth retardation (IUGR) is obtained by the treatment of dams with dexamethasone (100 µg/kg/day) during the third week of gestation. For the nutritional supplementation of gestating dams, lactoferrin will be given orally from the $15^{th}$ day of gestation to the weaning and food is available ad libitum. Lactoferrin will be delivered to newborn rats from postnatal day 1 until they will be weaned.

The following 6 groups of animals were used:
Group 1: Normal pups; no nutritional intervention in control dams (sham=osmotic pump with saline buffer).
Group 2: IUGR pups; no nutritional intervention in DEX treated dams.
Group 3: Normal pups; bLf supplementation (1 g/Kg/day) of control dams (sham) from the beginning of gestation to the end of the lactation.
Group 4: IUGR pups; bLf supplementation (1 g/Kg/day) of DEX treated dams from the beginning of gestation to the end of the lactation.
Group 5: IUGR pups; no nutritional intervention in DEX treated dams; vehicule (same volume as bLf) of pups were drop fed 200 mg/kg/day of a blend of amino acids mimicking casein protein in addition to lactation from 1 to 21 days after giving birth.
Group 6: IUGR pups; no nutritional intervention of DEX treated dams; bLf supplementation (200 mg/Kg/day) of pups by drop feeding in addition to lactation from 1 to 21 days after giving birth.

Figure 4A:
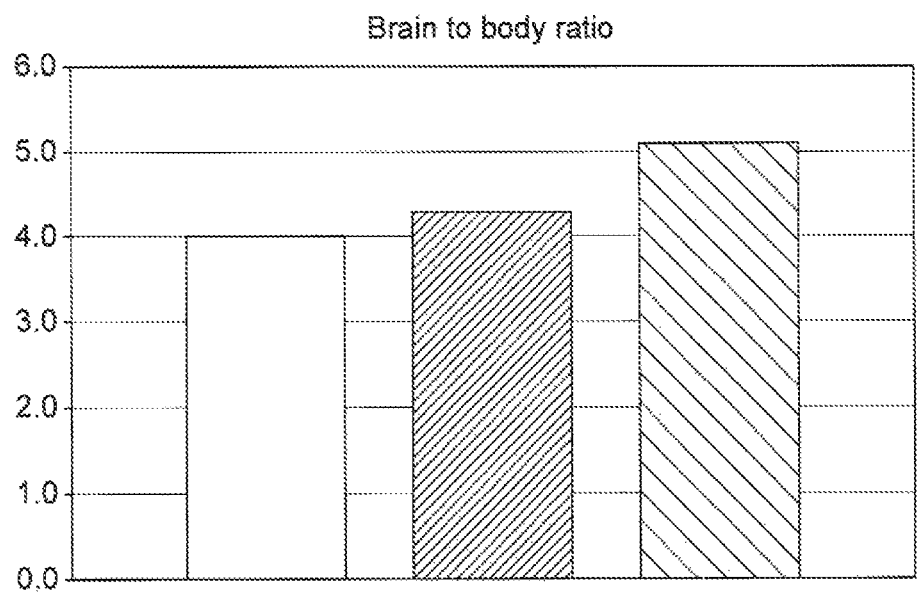
FIG. 4a shows the brain to body weight ratio at P1 in normal and IUGR infants. The brain to body weight ratio was found to be increased after lactoferrin administration during gestation, both in normal infants and even more in IUGR infants.
Figure 4B:
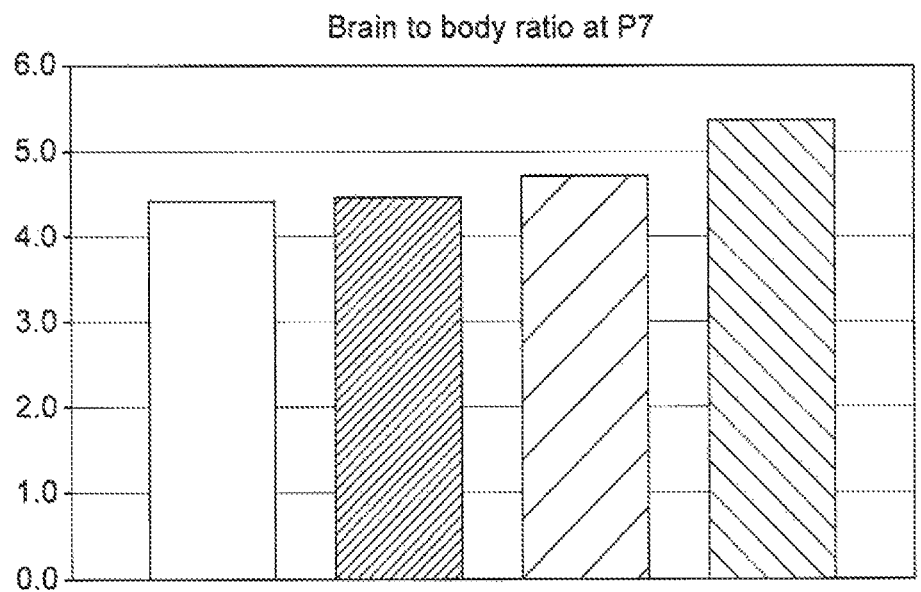
FIG. 4b shows the brain to body weight ratio at P7 in normal and IUGR infants. The brain to body weight ratio was found to be increased after lactoferrin administration, both in normal infants and even more in IUGR infants.

The results were the following and are shown in FIG. 4 *a*) and b).

The body weight of the offspring at birth of the DEX control and lactoferrin supplementation DEX are about 20-25% smaller than that control vehicule group. This shows that the DEX model is a valid tool to mimic a situation of frailty during the perinatal period in human species.

Thus this model is a property model to demonstrate the ability of lactoferrin to enhance the brain development apart from any other interventions.

Brain weight in both DEX control and DEX lactoferrin supplementation groups were smaller than that control vehicule group. However the decrease of brain weight is smaller than that body weight in Lf supplemented groups, thus brain to body weight ratio is bigger in Dex LF treatment compared to the Dex control group at postnatal day 1.

Interestingly the brain weight of the Dex Lf group caught up to the control vehicule group on postnatal day 21.

Lactoferrin Increases Metabolism in the Brain

Using LC model analysis, the following 18 metabolites will be quantified from both the cortex and hippocampus: alanine (Ala), aspartate (Asp), creatine (Cr), -aminobutyric acid (GABA), glucose (Glc), glutamate (Glu), glutamine (Gln), glutathione (GSH), glycerophosphorylcholine (GPC), phosphorylcholine (PCho), myo-inositol (Ins), lactate (Lac), N-acetylaspartate (NAA), N-acetylaspartylglutamate (NAAG), phosphocreatine (PCr), phosphorylethanolamine (PE), scyllo-inositol, and taurine (Tau).

It was aimed to visualize changes in cerebral development following adverse prenatal exposures using in vivo MR techniques (use of a 9.4 Tesla scanner at the EPFL), and to assess the effect of early nutritional interventions on brain development and metabolism mainly during the first month of life in our rodent models. Fast Spin-Echo (FSE) images and spectra edition $^1$H-MR Spectroscopy were used for the specific local cerebral and hippocampus metabolism. Briefly, FSE images (TR/TE=6000/80 ms; FOV=25×25 mm and matrix size=256×128) were realized to position MRS voxel of interest (VOI=1.5×1.5×2.5 mm3). First and second order shims were adjusted using FASTMAP [Martin E, 2001, Ann Neurol 49:518-521]. The water linewidths ranged between 8 and 15

Hz. Spectra acquisitions both within the cortical lesion and the contralateral cortical area were performed using an ultra-short echo time (TE/TR=2.7/4000 ms) SPECIAL spectroscopy method. This method combines 1D image-selected in vivo spectroscopy (ISIS) in the vertical (Y) direction with a slice selective spin echo in the X and Z directions and provides full signal intensity available in the excited region. 35 to 70 series of FIDs (12 averages each) were acquired, individually corrected for frequency drift, summed together and corrected for residual eddy current effects using the reference water signal.

Figure 5:
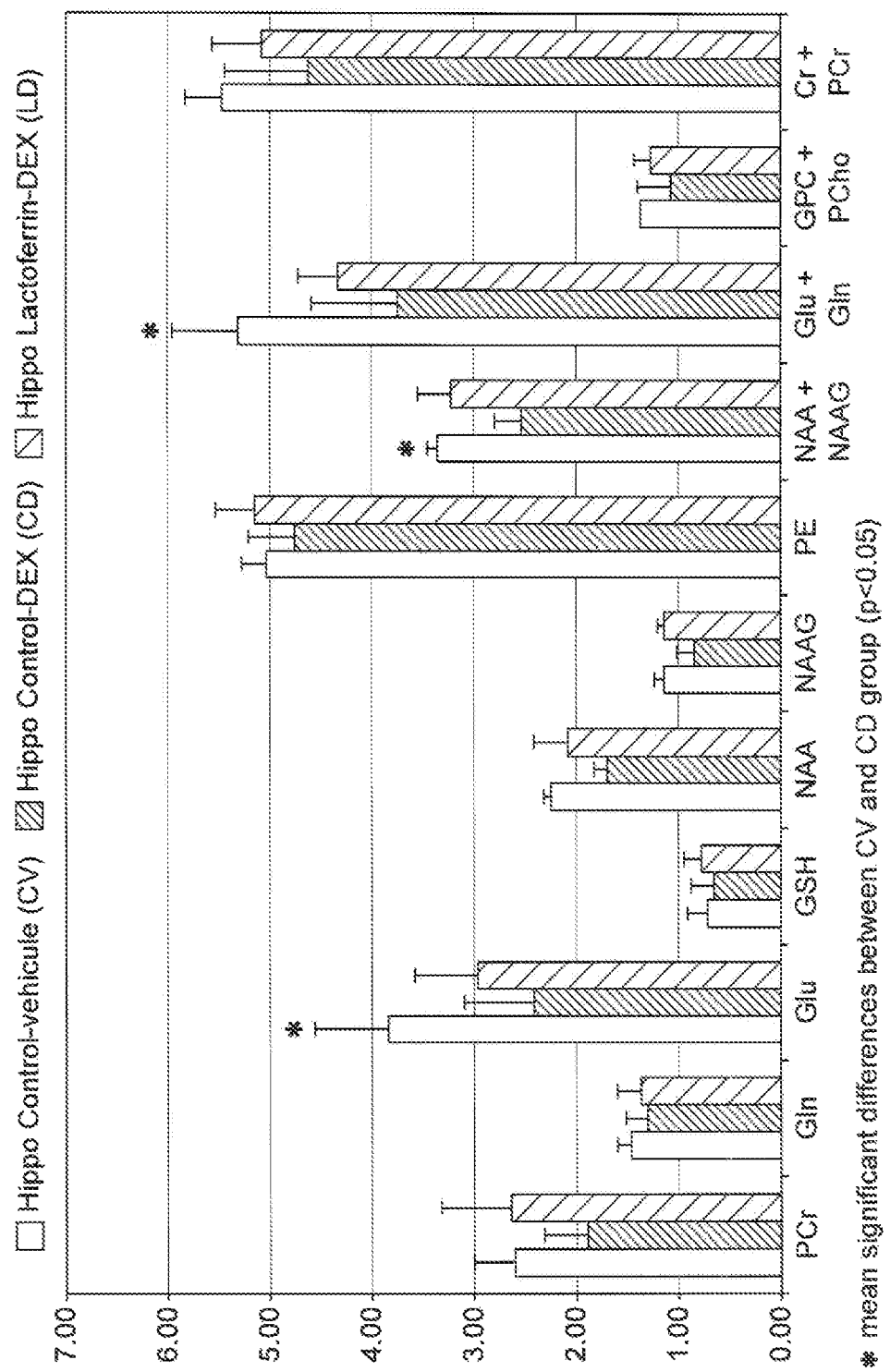
FIG. 5 shows the presence of several metabolic markers indicative for brain activity and development in the hippocampus of normal infants, IUGR infants and IUGR infants treated with lactoferrin at P7. Hippocampal activity is linked to learning and short term memory.
Figure 6:
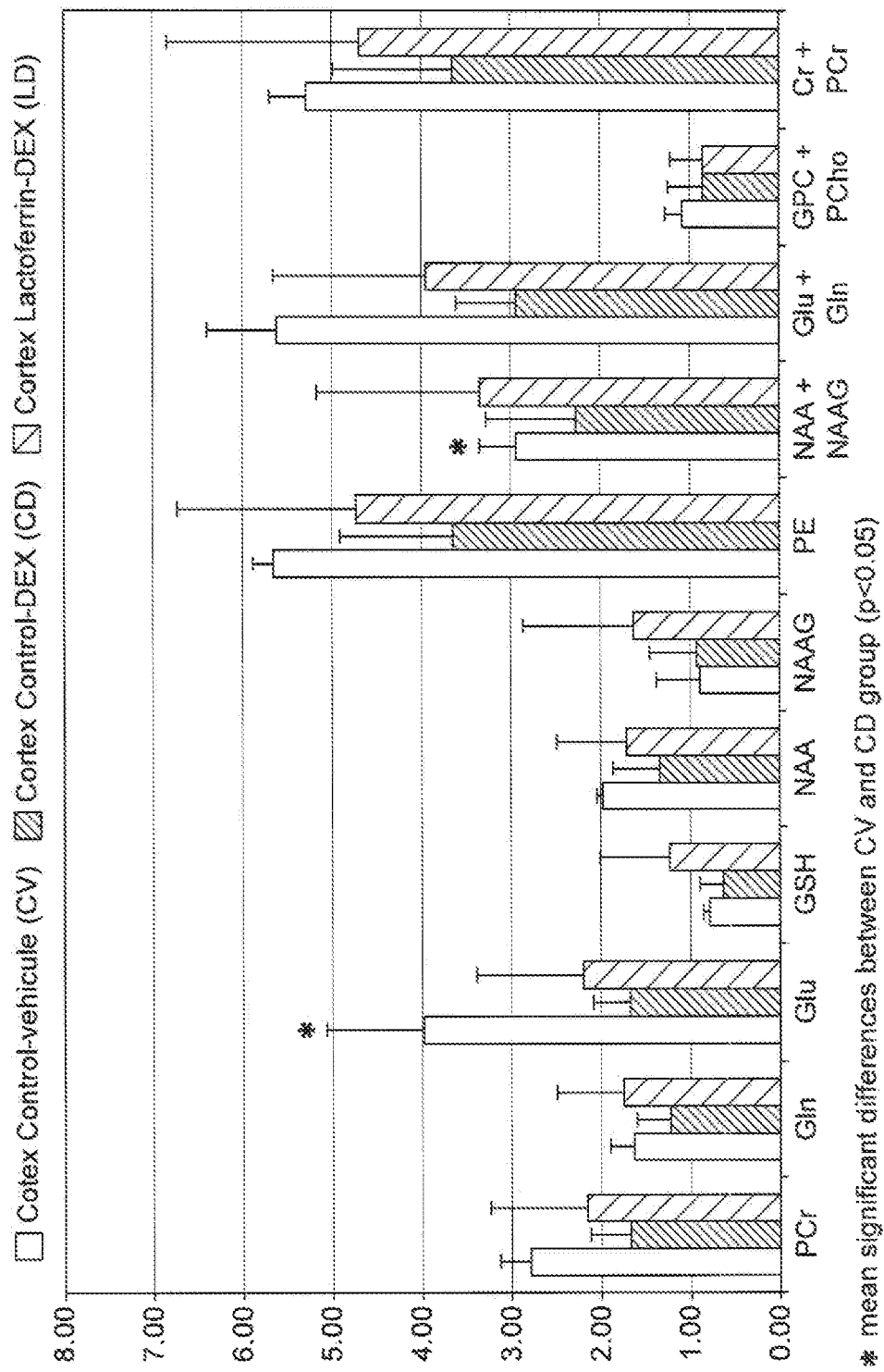
FIG. 6 shows the presence of several metabolic markers indicative for brain activity and development in the cortex of normal infants, IUGR infants and IUGR infants treated with lactoferrin at P7. Cortex activity is linked to long term memory.

The results were the following and are shown in FIG. 5 and FIG. 6.

There are significant differences in phosphocreatine (PCr), N-acetylaspartylguatamate (NAAG), N-acetylaspartate (NAA), NAA+NAAG and creatine (Cr)+phosphocreatine (PCr) concentration between control vehicle (n=5) and control Dex pups (n=4) at 7 days after giving birth (P<0.05~0.01). LF treatment Dex pup group (n=6) however, had a trend to reverse the concentrations of above metabolic markers found in Contr-Dex group at P7, but differences did not reach statistic significant in both hippocampus and cortex.

N-Acetylaspartate (NAA), or N-acetylaspartic acid, is a derivative of aspartic acid with a formula of $C_6H_9NO_5$ and a molecular weight of 175.139. NAA is the second most concentrated molecule in the brain after the amino acid glutamate. NAA is synthesized in neurons from the amino acid aspartate and acetyl coenzyme A. Its proposed primary functions include:

- it is a source of acetate for lipid and myelin synthesis in oligodendrocytes, the glial cells that myelinate neuronal axons
- it is a precursor for the synthesis of the important neuronal dipeptide N-Acetylaspartylglutamate
- it is a neuronal osmolyte that is involved in fluid balance in the brain
- NAA may also be involved in energy production from the amino acid glutamate in neuronal mitochondria The NAA signal reflects tissue concentrations of both NAA and N-acetylaspartylglutamate (NAAG). NAA has been reported to reflect the presence of neurons, oligodendroglial lineage cells, and axons in the CNS (Urenjak J, 1993, J Neurosci 13:981-989; Martin E, 2001, Ann Neurol 49:518-521; Bjartmar C, 2002, Ann Neurol 51:51-58). It has been suggested that NAA(G) may be an acetyl-group carrier between mitochondria and cytoplasm in neuronal cells (Patel T B, 1979, Biochem J 184:539-546; Truckenmiller M E, 1985, J Neurochem 45:1658-1662). A decrease of the NAA signal is usually interpreted as a reduction in the number of neurons, but it may also reflect altered function of neuronal mitochondria. The increase of NAA/Cho ratios in cerebral tissue as a result of maturation was previously described in detail and is confirmed in the present study (van der Knaap M S, 1990, Radiology 176:509-515; Kreis R, 2002, Magn Reson Med 48:949-958).

N-Acetylaspartylglutamic acid (N-acetylaspartyl-glutamate or NAAG) is a neuropeptide which is the third-most-prevalent neurotransmitter in the mammalian nervous system. NAAG consists of N-acetylaspartic acid (NAA) and glutamic acid coupled via a peptide bond. NAAG was discovered as a nervous system-specific peptide in 1965 by Curatolo and colleagues (Isaacks R E, 1994, Neurochem Res 19:331-338) but was not extensively studied for nearly 20 years. It meets the criteria for a neurotransmitter, including being concentrated in neurons, packed in synaptic vesicles, released in a calcium-dependent manner, and hydrolyzed in the synaptic space by enzymatic activity. NAAG activates a specific receptor, the metabotropic glutamate receptor type 3. It is synthesized enzymatically from its two precursors and catabolized by NAAG peptidases in the synapse. The inhibition of the latter enzymes has potentially important therapeutic effects in animal models of several neurologic conditions and disorders.

myo-Inositol is a crucial constituent of living cells and participates in several physiologic functions. It is a major osmolyte and also serves as the precursor to phosphatidylinositol. myo-inositol has been used as a glial cell marker (Isaacks R E, 1994, Neurochem Res 19:331-338). Lac may be used as fuel for the brain but also for the synthesis of myelin (Sanchez-Abarca L I, 2001, Glia 36:321-329).

A decrease of the N-acetylaspartate/choline (NAA/Cho) ratio in asphyxiated full-term neonates predicts an adverse neurodevelopmental outcome (Groenendaal F, 1994, Pediatr Res 35:148-151; Peden C J, 1993, Dev Med Child Neurol 35:502-510; Roelants-van Rijn A M, 2001, Pediatr Res 49:356-362). Myo-inositol (ml), which is one of the osmo-regulators of the brain, can be found in astrocytes and is considered a glial cell marker (Isaacks R E, 1994, Neurochem Res 19:331-338).

Lactoferrin improves neuron density and neuron survival and is able to repair and/or reverse neuronal cell damage.

A morphological examination was conducted following MR acquisition. Contiguous sections at the level of the striatum, dorsal and lateral hippocampus were collected to assess cortical and hippocampal architecture and white matter injury. Specific cells types were labeled using immunohistochemistry, in order to determine specific cellular responses. Specific labeling of neurons (NeuN), astrocytes (GFAP) and radial glia (Nestin), in conjunction with markers of white matter myelination (MBP), was performed. The brief methodology was the followings:

At P7 and P21, respectively, pups from each group were deeply anesthetized using ketalar (50 mg/ml; 0.2-0.5 ml, i.p.). Animals were perfused intracardially with 0.9% NaCl, then 4% paraformaldehyde. Brains were removed, weighed and postfixed in 4% paraformaldehyde overnight, then 30% sucrose for 24 h minimum, and stored at −80° C. until sectioned. Coronal sections (10 μm) at the level of the dorsal hippocampus were cut on a cryostat (Microm Cryo-Star HM 560M, Microm International, Germany). Three sections at 200 μm intervals were collected from each animal.

Immunohistochemitry: Brain tissue was processed for immunoreactivity to MBP (1:400 brand city country) using the avidin-biotin peroxidase complex (ABC; Vector Laboratories, Burlingame, Calif., USA). Sections were blocked in 4% bovine serum albumin (BSA brand city country), then incubated with the primary antibody for 24 h at 4° C., after which they were incubated with the secondary antibody (1:200 brand city country), then with the avidin-biotin complex (1:200, Vector Laboratories, Burlingame, Calif., USA). Sections were reacted with the chromagen, 3,3-diaminobenzidine (DAB brand city country) in 0.01% hydrogen peroxide, then coverslipped.

The same protocol was used for fluorescence immunohistochemistry for nestin (1:500 brand city country), GFAP (1:400 brand city country), and NeuN (1:200 brand city country), except that sections were not incubated in the avidin-biotin complex and DAB.

Each experimental group and their respective controls were stained simultaneously. When the primary antibody treatment was omitted, staining failed to occur.

Quantitative analyses were performed using MetaMorph® Imaging System (Meta Imaging Software, Molecular Devices Corporation, Pennsylvania, U.S.A). Values for each animal were pooled and a mean of means±SEM was calculated for each group. Measurements were made on coded slides blinded to the observer with the codes not being disclosed until the conclusion of analyses.

Figure 7:
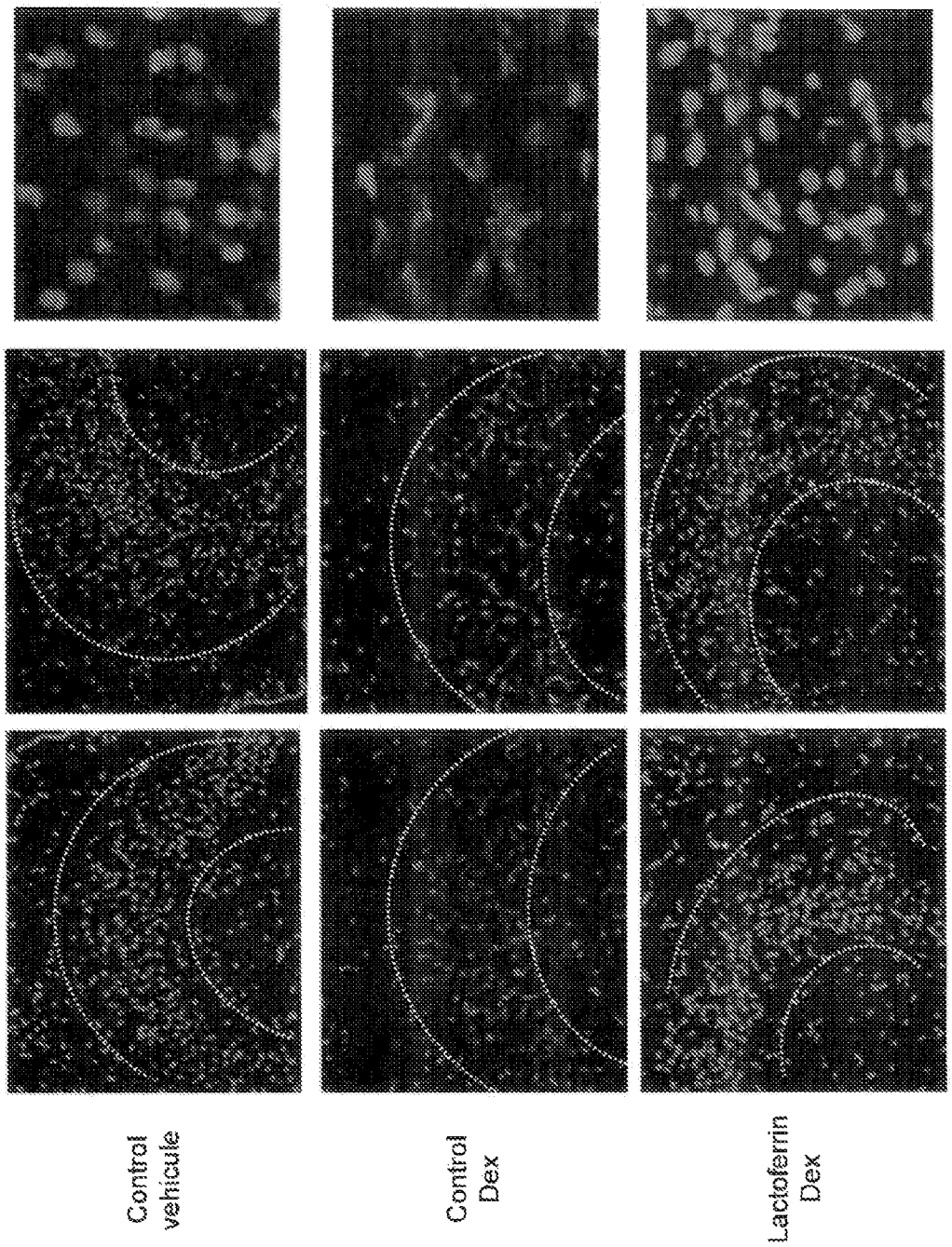
FIG. 7 shows the nuclei morphology in the CA2-CA3 field of the hippocampus after DAPI staining.

The results were the following and are shown in FIG. 7

The histological analysis revealed that LF supplementation Dex pup (n=5) has significant increased the Nuclei morphology and neuron density in the CA2-CA3 field of the hippocampus compared to the Dex control pup at P7. A decrease in neuronal density in the cortex at P7 suggests neuronal loss. The neuronal density is similar to the normal control vehicle group (FIG. 7). Lactoferrin given in this particular developmental time frame will influence neuronal density in the hippocampus and area of great vulnerability for undernutrition and stress related brain abnormalities. This implies that LF administration increases neuron survival and neuron protection, for example in a young IUGR rat.

Lactoferrin supplementation increases gene expression of Brain derived neutrophic factor (BDNF).

Figure 8:
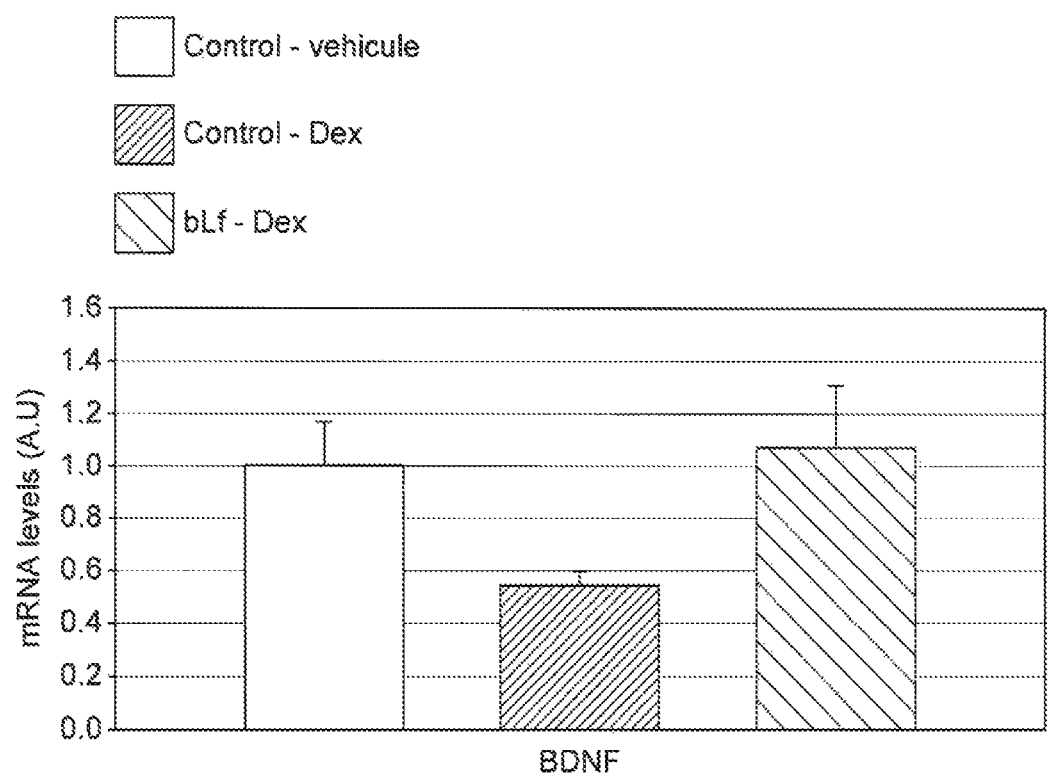
FIG. 8 shows that dietary lactoferrin supplementation significantly increased gene expression of brain derived neutrophic factor (BDNF) at postnatal day 7.

FIG. 8 shows that dietary lactoferrin supplementation significantly increased gene expression of brain derived neutrophic factor (BDNF) at postnatal day 7.

BDNF is a neurotrophic factor that promotes neuronal differentiation, survival, and plasticity in the peripheral nervous system and central nervous system (CNS). It is a key molecule involved in many neuronal aspects of developing and mature neurons. In CNS, BDNF elicits long-term potentiation, which is related to synaptic plasticity. BDNF promotes neurogenesis. In particular, BDNF promotes the outgrowth of neurites and increases the expression of synaptic proteins, which are required for establishing synaptic connections or functions during development. Thus dietary lactoferrin has a role of both neurodevelopment and neuroprotection.

Gene expression is the process by which the information encoded by a gene is converted into a protein. Our study is the first to analyze effect of lactoferrin supplementation on gemonic analysis brain BDNF level using a well established method.

Briefly, total RNA from hippocampus was extracted using the RNeasy Mini Kit® according to the manufacturer's protocol (Qiagen, Basel, Switzerland). 2.5 micrograms total RNA were reverse-transcribed using 800 units of Moloney murine leukemia virus reverse transcriptase (Invitrogen, Basel, Switzerland), in the presence of 0.3 units/microl RNAsin (Promega Corp, Madison, Wis.), 7.5 microM of random primers (oligo(dN)6), 1.2 mM dNTP and 12 microM of DTT. The expression of the cDNAs for rat BDNF were determined by quantitative real-time PCR using an ABI step one plus Detection System (Applera Europe, Rotkreuz, Switzerland) and were normalized using the housekeeping ribosomal gene 36B4. PCR products were quantified using the SYBR Green Core Reagent kit (Applera Europe, Rotkreuz, Switzerland) and results are expressed in arbitrary units (A.U) relative to control group values. Primers were designed using the Primer Express software (Applera Europe, Rotkreuz, Switzerland).

Animal Behavior Data:

Bovine milk lactoferrin (bLF) was supplemented to the rat mother throughout gestation and lactation (total 6 weeks) at a dose level of 1 g/kg/day to determine the benefits of bLF on animals behavior in 4 different groups: (1) control-vehicle (CE); (2) control-DEX (CD); (3) lactoferrin-vehicle (LE) and; (4) lactoferrin-Dex (LD) at the age 4.5 months using an Intellicage.

The free adaptation test (relevant to open field test) was to place rats into the Intellicage, a new environment for 3 days to monitor the rat's movement and interaction with the environment (number of visits different of the corners). The exploratory behavior/curiosity were monitored to analyze how the rats adapted to the new environment.

The results showed that control DEX rats had a decreased exploratory activity/curiosity with the Intellicage compared to the control-vehicle (normal control), bLF-vehicle and bLF-DEX rats throughout the 3 days trail. The differences between control-Dex and both the control-vehicle and bLf-Dex are significant at day 3 of the free adaptation trail (P<0.05). These results suggested that prenatal LF supplementation improved the anxiety-like behavior, including more exploratory activity, curiosity and interaction to the new environment for the healthy and early life brain injured adult animals at age 4.5 months old. The obtained data suggest a pronounced neuron protective effect of LF and a somewhat smaller effect on neurodevelopment (FIG. 1).

The invention claimed is:

1. A method for use in the treatment of a delayed brain development and/or a delayed development of the nervous system comprising administering a composition comprising lactoferrin in a concentration of 2 g-25 g/100 kcal of the composition to an individual in need of same.

2. A method for use in the repair of a delayed brain development and/or a delayed development of the nervous system comprising administering a composition comprising lactoferrin in a concentration of 2 g-25 g/100 kcal of the composition to an individual in need of same.

3. A method for use in the treatment of a delayed vision development, a delayed neural migration, and/or a delayed cognitive development comprising administering a composition comprising lactoferrin in a concentration of 2 g-25 g/100 kcal of the composition to an individual in need of same.

4. A method for use in the treatment of an impaired learning ability, an impaired mental performance, an impaired memory or a reduced attention span comprising administering a composition comprising lactoferrin in a concentration of 2 g-25 g/100 kcal of the composition to an individual in need of same.

5. A method in accordance with claim 1, wherein the composition is to be administered to an individual selected from the group consisting of mothers during pregnancy, mothers during lactation, premature or term born babies, infants, toddlers, children and teenagers.

6. A method in accordance with claim 2, wherein the composition is to be administered to an individual selected from the group consisting of mothers during pregnancy, mothers during lactation, premature or term born babies, infants, toddlers, children and teenagers.

7. A method in accordance with claim 3, wherein the composition is to be administered to an individual selected from the group consisting of mothers during pregnancy, mothers during lactation, premature or term born babies, infants, toddlers, children and teenagers.

8. A method in accordance with claim 4, wherein the composition is to be administered to an individual selected from the group consisting of mothers during pregnancy, mothers during lactation, premature or term born babies, infants, toddlers, children and teenagers.

9. Method of claim 1, wherein the composition is administered to provide at least 0.2 g lactoferrin per kg of body weight of the individual per day.

10. Method of claim 1, wherein the composition is administered to provide at least 1 g lactoferrin per kg of body weight of the individual per day.

11. Method of claim 1, wherein the individual to whom the composition is administered has a delayed brain development and/or a delayed development of the nervous system.

12. Method of claim 3, wherein the individual to whom the composition is administered has a delayed vision development, a delayed neural migration, and/or a delayed cognitive development.

13. Method of claim 3, wherein the individual to whom the composition is administered has an impaired learning ability, an impaired mental performance, an impaired memory or a reduced attention span.

\* \* \* \* \*